(12) United States Patent
Cedergreen et al.

(10) Patent No.: US 10,235,729 B1
(45) Date of Patent: Mar. 19, 2019

(54) METHODS AND SYSTEMS FOR PREFERRED PHARMACY DESIGNATION

(71) Applicant: Express Scripts, Inc., St. Louis, MO (US)

(72) Inventors: Jacob Jon Cedergreen, Saint Louis, MO (US); Katherine Harini Sundararaman, St. Louis, MO (US); Christopher Ray Fowler, Webster Groves, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 257 days.

(21) Appl. No.: 13/790,090

(22) Filed: Mar. 8, 2013

Related U.S. Application Data

(60) Provisional application No. 61/608,264, filed on Mar. 8, 2012.

(51) Int. Cl.
*G06Q 30/02* (2012.01)
*G06Q 50/22* (2018.01)

(52) U.S. Cl.
CPC ......... *G06Q 50/22* (2013.01); *G06Q 30/0226* (2013.01)

(58) Field of Classification Search
None
See application file for complete search history.

(56) References Cited

U.S. PATENT DOCUMENTS

| 8,639,523 | B1* | 1/2014 | Pinsonneault | G06Q 10/10 |
| | | | | 705/14.36 |
| 2004/0153336 | A1* | 8/2004 | Virdee et al. | 705/2 |
| 2004/0260577 | A1* | 12/2004 | Dahlin | G06F 19/00 |
| | | | | 705/2 |
| 2007/0250341 | A1* | 10/2007 | Howe et al. | 705/2 |
| 2009/0089083 | A1* | 4/2009 | Paradis | G06Q 10/00 |
| | | | | 705/2 |
| 2010/0057489 | A1* | 3/2010 | Howe | G06F 19/328 |
| | | | | 705/2 |
| 2010/0088168 | A1* | 4/2010 | Sullivan | B65D 27/00 |
| | | | | 705/14.17 |
| 2010/0145726 | A1* | 6/2010 | Duke | G16H 50/20 |
| | | | | 705/3 |

(Continued)

OTHER PUBLICATIONS

Prime Therapeutics, Products & Services, Web Page [online], [available on Feb. 12, 2010]. Retrieved from the Internet <URL: https://web.archive.org/web/20100212191154/http://www.primetherapeutics.com/networks.html>.*

(Continued)

*Primary Examiner* — Neal Sereboff
(74) *Attorney, Agent, or Firm* — Husch Blackwell LLP

(57) ABSTRACT

Methods and systems for managing pricing guarantees for prescription drugs are described. In one embodiment, a designation of a pharmacy within a pharmacy network may be received as a preferred pharmacy designation. The preferred pharmacy designation may be associated with a member. A set of preferred pharmacy benefits may be associated with the member and the preferred pharmacy designation. A pharmacy claim associated with the preferred pharmacy designation for a prescription for the member may be adjudicated based on the set of preferred pharmacy benefits. Other methods and systems are described.

27 Claims, 5 Drawing Sheets

(56) References Cited

U.S. PATENT DOCUMENTS

2012/0109839 A1* 5/2012 Anderson et al. ............ 705/322

OTHER PUBLICATIONS

Causey, Lisa, "Nuts and Bolts of Pharmacy Reimbursement: Why it Should Matter to You," Health Law Perspectives (Jun. 2009).*
Balto, David "The Need fo Greater Fee Disclosure Among the PBM Industry" Testimony Before the Employee Benefits Security Administration—U.S. Department of Labor Dec. 7, 2010.*
French, Zachary "In Walgreens Dispute, Express Scripts Seeks Knockout Blow to Pharmacies—and Patients" Jul. 7, 2011 Pharmacy Benefits Managers (Not Prior Art).*
Garis et al., "Examining the value of pharmacy benefit management companies" Pharmacy Benefit Management—Am J Health—Syst Pharm 2004.; 61:81-5.*
Bernedt at al., "Pricing and Reimbursement in U.S. Pharmaceutical Markets" Harvad School—NBER Working Paper Series—Sep. 2010.*
Aetna, "Pharmacy 101—Your Pharmacy Benefits Guide" 05.03.376.1 A (9/10) (Year: 2010).*
Bisping, Todd, (2010) "Caterpillar Breaks New Ground Managing the Prescription Drug Supply Chain" American Journal of Pharmacy Benefits published online (Year: 2010).*
Definition—"Preferred Pharmacy" As downloaded on Jan. 11, 2018 (Year: 2018).*
Aetna, "Benefits Summary," MRI Contract Staffing 800469, Dec. 18, 2007, pp. 1-10.
BlueCross BlueShield, Federal Employee Program, Oct. 2009, pp. 1-2.
BlueCross BlueShield of Mexico, "2010 Blue MedicareRX (PDF) Decision Guide," Aug. 2009, pp. 1-18.
Miller, "Preferred Pharmacy Networks Can Cut Costs," http://www.shrm.org/hrdisciplines/benefits/Articles/Pages/PharmacyNetworks.aspx, pp. 1-2.
Grossomanides, "Advanced Pharmacy Concepts," http://www.apc-rx.com/blog/client/index.cfm/2011/1/24/News-from-CMS--Week-of-January-24-2011, downloaded Mar. 8, 2013, pp. 1-6.
"How Align Pharmaceutical Benefits Work / Align," http://align.restat.com/how-it-works/, downloaded Mar. 8, 2013, pp. 1.
"CVS' New "Pharmacy Home" Plan—Yahoo! Finance," http://finance.yahoo.com/news/cvs-pharmacy-home-plan-154521328.html, downloaded Mar. 8, 2013, pp. 1-2.

* cited by examiner

METHODS AND SYSTEMS FOR PREFERRED PHARMACY DESIGNATION

CROSS-REFERENCE TO A RELATED APPLICATION

This application claims the benefit of U.S. provisional patent application 61/608,264, filed on 8 Mar. 2012, entitled "Methods and Systems for Preferred Pharmacy Designation," the entire disclosure of which is incorporated herein by reference.

FIELD

The field relates to pharmacy benefit plans, and more particularly to facilitating member preferred pharmacy designation.

BACKGROUND

Pharmacy benefit managers generally provide prescription drug programs for clients that may, for example, sponsor drug benefit programs for members. As part of the providing the prescription drug programs for clients, pharmacy benefit managers (PBM's) may adjudicate claims from pharmacies for prescriptions filled by members at various pharmacies. The PBM may also reimburse the pharmacies for prescriptions obtained by members at the pharmacies. The PBM may also bill clients for the cost of prescriptions adjudicated by the pharmacy benefit manager.

DETAILED DESCRIPTION

Figure 1:
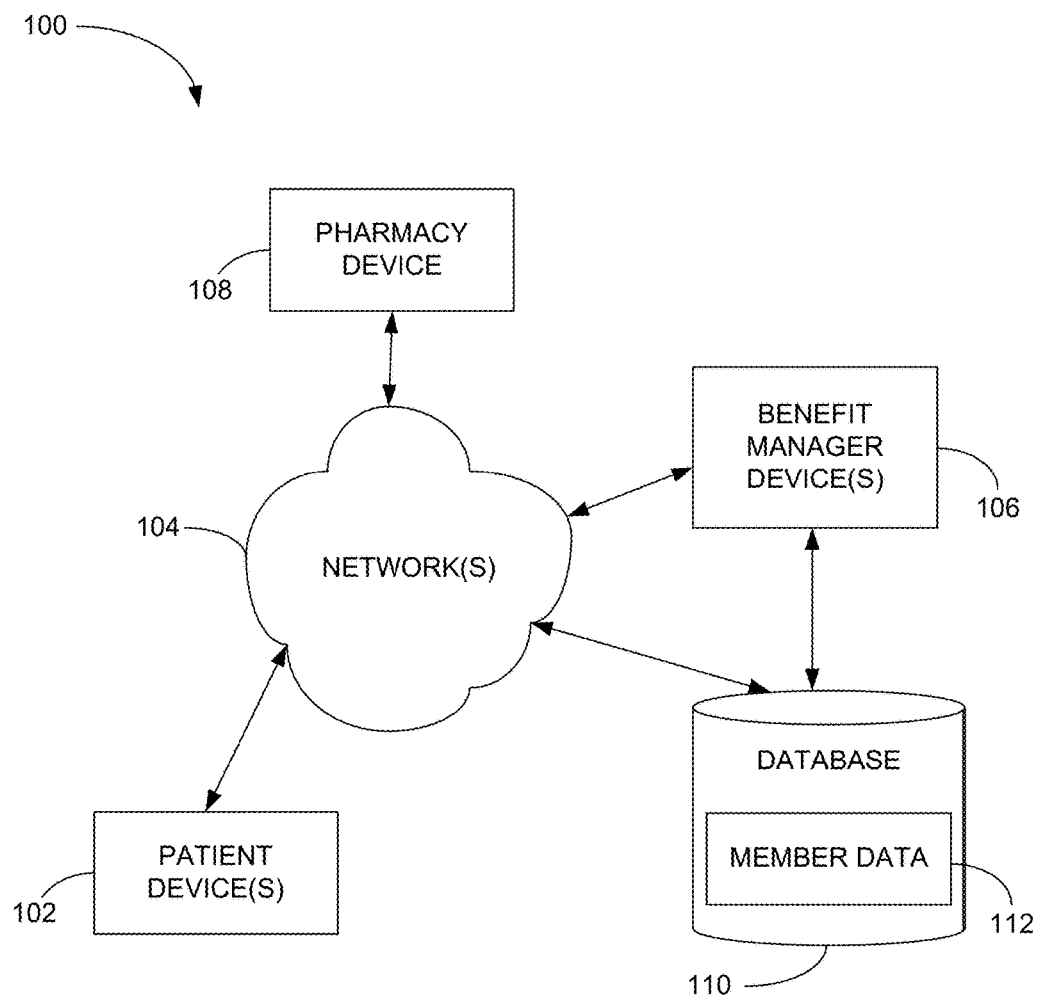
FIG. 1 is a block diagram of an example system, according to an example embodiment.

Example methods and systems for preferred pharmacy designation are described. In the following description, for purposes of explanation, numerous specific details are set forth in order to provide a thorough understanding of example embodiments. It will be evident, however, to one of ordinary skill in the art that embodiments of the invention may be practiced without these specific details.

In general, a client engages a pharmacy benefit manager (PBM) to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. A person who is a participant or member of a drug benefit program offered by the client may obtain prescription drugs according to pricing, pharmacy selection, rebates, discounts and the like provided by the terms of the drug benefit program.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company.

Some of the operations of the PBM may include the following. A member or a person acting on behalf of the member attempts to obtain a prescription drug at a retail pharmacy location of a pharmacy where the member can obtain drugs in a physical store from a pharmacist or pharmacist technician. The pharmacy can be associated with a single retail pharmacy location, or can be a pharmacy chain that includes multiple retail pharmacy locations. The pharmacy then submits a claim to the PBM for the prescription drug. The PBM performs certain adjudication operations including verifying the eligibility of the member, reviewing the formulary to determine appropriate co-pay, coinsurance, and deductible for the prescription drug, and performing a drug utilization review (DUR) on the member. The PBM then provides a response to the pharmacy following performance of the aforementioned operations. The aforementioned adjudication operations generally occur before the co-pay is received and the prescription drug dispensed. However, the operations may occur simultaneously, substantially simultaneously, or in a different order. In addition, more or less adjudication functions may be performed as part of the adjudication process.

As part of the adjudication, the client (or typically the PBM on behalf of the client) ultimately reimburses the pharmacy for filling the prescription drug when the prescription drug was successfully adjudicated. The amount of reimbursement paid to the pharmacy by the client and/or PBM may be based at least in part on the type of pharmacy network in which the pharmacy is included. Other factors may be used to determine the reimbursement amount in addition to the type of pharmacy network. In an embodiment in which the PBM reimburses the pharmacy on behalf of the client, the PBM may subsequently bill the client for the amount of the reimbursement, and typically also for the services of the PBM in adjudicating the claim and otherwise managing the drug benefit program. The amount that the client is billed by the PBM may be based at least in part on the reimbursement paid to the pharmacy, the type of pharmacy network in which the pharmacy is included. Other factors may be used to determine the billed amount.

In some embodiments, a member of a drug benefit program may designate a particular pharmacy, or in some cases a particular pharmacist, as being a preferred pharmacy. The pharmacy designated by the member as being the preferred pharmacy may include a pharmacy and/or a pharmacist that the member wishes to primarily utilize for filling prescriptions, or for other related services. For example, the pharmacy designated as a preferred pharmacy for the member may include a retail pharmacy that is geographically convenient for the member, or a retail pharmacy for which the member has an affinity, for any other reason.

In some embodiments, the benefits that the member receives when utilizing the preferred pharmacy (or preferred pharmacist) may differ in at least some regard from the benefits that the member receives when using another pharmacy and/or pharmacist, which has not been designated as the preferred pharmacy and/or pharmacist for the member. For example, the member may be required to pay a lower co-pay for prescriptions at his preferred pharmacy and/or with his preferred pharmacist as compared to the co-pay required by the member at other, non-preferred, pharmacies and/or pharmacists. In other examples, the benefits that the member may receive at the preferred pharmacy may include higher levels of coverage under the drug benefit program for vaccinations, complimentary, or lower priced, therapy consultation, complimentary, or lower priced, screenings (e.g., blood pressure screenings, blood sugar screenings, cholesterol screenings, or the like). The member may further receive various other additional and/or alternative benefits when utilizing the preferred pharmacy and/or pharmacist, that may be different than at least some of the benefits that the member receives when utilizing another (i.e., not the preferred) pharmacy and/or pharmacist.

In some embodiments, the PBM providing the drug benefit program for the member may be able to achieve lower reimbursements rates for prescriptions, or other services covered under the drug benefit program, from the preferred pharmacy associated with the member and/or through a pharmacist associated with the preferred pharmacy. For example, the pharmacy may be willing to negotiate lower reimbursement rates with the PBM for members that have designated the pharmacy as a preferred pharmacy on the basis that the member may be more likely to utilize the pharmacy for products and/or services other than prescriptions. For example, in consideration of the member's affinity for the pharmacy (e.g., based on the member designating the pharmacy as the member's preferred pharmacy) it may be more likely that the member may utilize the pharmacy for over the counter medications, services such health screenings (e.g., blood pressure screenings, blood sugar screenings, cholesterol screenings, or the like). In some embodiments, the member may develop a greater relationship with a pharmacist, thereby developing more trust in the pharmacist and increasing the member's likelihood of adherence with a prescription drug treatment regimen. Further, on the basis of the member designating the pharmacy as a his preferred pharmacy, it may be anticipated that the member will utilize the pharmacy for a majority of his prescriptions, thereby increasing the likelihood of a certain projected volume of business for the pharmacy from the member. Further, in the aggregate, if multiple members (within a single drug benefit program and/or across multiple different drug benefit programs, which may be sponsored by more than one client of the PBM) have designated the same pharmacy as being their preferred pharmacy, the anticipated volume by all of the members that have designated the pharmacy as their preferred pharmacy may allow the PBM to negotiate a lower reimbursement rate with the pharmacy.

FIG. 1 is a block diagram of an example system 100, according to an example embodiment. The system 100 is an example embodiment in which a pricing discount for prescription drugs may be managed. The system 100 includes a patient device 102 in communication with a benefit manager device 106 over a network 104. The system may also include a pharmacy device 108.

The patient device 102 is used by a device operator. The device operator may be a member of a drug benefit program. However, the device operator may be another person operating the patient device 102 on behalf of the member. Examples of such people include parents, guardians and caregivers. Accordingly, while some illustrative embodiments may be described herein in which the device operator may be the member, it should be appreciated that the device operator may be an individual other than the member.

In some embodiments, the member may utilize the patient device 102 to designate a pharmacy as a preferred pharmacy for the member. The patient device 102 may be a stand-alone device that solely provides at least some of the functionality to enable the designation of a preferred pharmacy for a member, or may be a multi-use device that has functionality outside of enabling the designation of a preferred pharmacy for a member as described herein. Examples of the patient device 102 include a set-top box (STB), a receiver card, a mobile telephone, a personal digital assistant (PDA), a display device, a portable gaming unit, a smart prescription drug cap or capper, and a computing system; however other devices may also be used. In some embodiments, the computing system. For example, the patient device 102 may include a mobile electronic device, such an IPHONE or IPAD device by Apple, Inc., mobile electronic devices powered by ANDROID by Google, Inc., and a BLACKBERRY device by Research In Motion Limited. The patient device 102 may also include other computing devices, such as desktop computing devices, notebook computing devices, netbook computing devices, gaming devices, and the like. Other types of electronic devices may also be used.

The network 104 by which the patient device 102 communicates with the benefit manager device 106, and/or the pharmacy device 108 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for the management of a drug benefit program. While the entity operating the benefit manager device 106 is typically a PBM, other entities may operate the benefit manager device 106 either on behalf of themselves, the PBM, or another entity. In some embodiments, a PBM that provides the drug benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary to determine appropriate co-pay, coinsurance, and deductible for the prescription drug, and performing a DUR on the member. The PBM then provides a response to the pharmacy following performance of the aforementioned operations. As part of the adjudication, the client (or the PBM on behalf of the client) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as part of the adjudication process.

The patient device 102 may be in a client-server relationship with the benefit manager device 106, a peer-to-peer relationship with the benefit manager device 106, and/or in a different type of relationship with the benefit manager device 106.

The pharmacy device 108 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy device 108 may be utilized by the pharmacy to submit the claim to the PBM for adjudication. Additionally, in some embodiments, the pharmacy device 108 may enable information exchange between the pharmacy and the PBM, for example, to allow the sharing of member information such as drug history, and the like, that may allow the pharmacy to better service a member (e.g., by providing more informed therapy consultation and drug interaction information, etc.).

The benefit manager device 106 may be in communication directly (e.g., through local storage) and/or through the network 104 (e.g., in a cloud configuration or software-as-a-service) with a device that stores a database 110. The database 110 may be deployed on the patient device 102, the benefit manager device 106, both the patient device 102 and the benefit manager device 106, partially on the patient device 102 and partially on the benefit manager device 106, on a separate device, or may otherwise be deployed. The database 110 may store member data 112.

The member data 112 includes information regarding members of the pharmacy benefit plan. In general, the member data 112 may include member identification, member prescription data (e.g., prescribed drugs, prescription history, pharmacy usage, and the like), member health screening information, and the like.

While the system 100 in FIG. 1 is shown to include single devices 102, 106, 108 multiple devices may be used. The devices 102, 106, 108 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102, 106, 108 or in parallel to link the devices 102, 106, 108.

Figure 2:
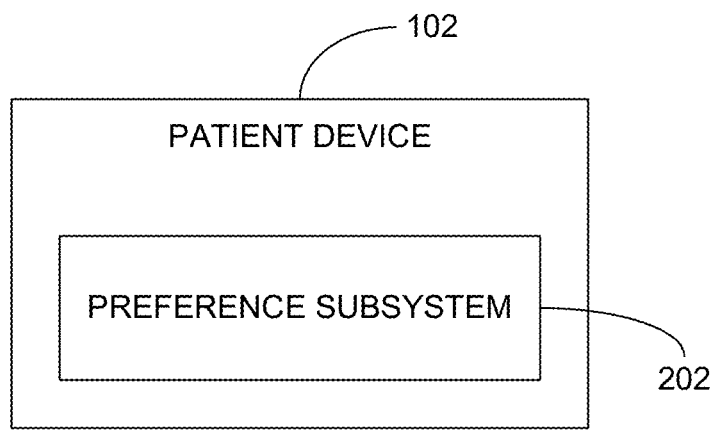
FIG. 2 is a block diagram of an example patient device that may be deployed within the system of FIG. 1, according to an example embodiment.

FIG. 2 illustrates the patient device 102, according to an example embodiment. The patient device 102 may be used by a device operator to designate a preferred pharmacy and/or pharmacist for a member. The patient device 102 may be deployed in the system 100, or may otherwise be used.

The patient device 102 may include a preference subsystem 202. The preference subsystem 202 may enable a preferred pharmacy and/or pharmacist to be designated for the member and for various benefits under a drug benefit program to be associated with the preferred pharmacy and/or pharmacist and the member.

Figure 3:
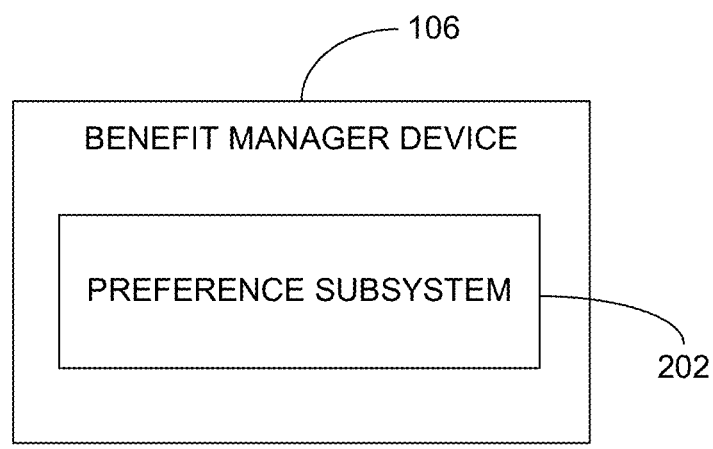
FIG. 3 is a block diagram of an example benefit manager device that may be deployed within the system of FIG. 1, according to an example embodiment.

FIG. 3 illustrates the benefit manager device 106, according to an example embodiment. The benefit manager device 106 may be deployed in the system 100, or may otherwise be used.

The benefit manager device 106 may include the preference subsystem 202. In some embodiments, the preference subsystem 202, when used, may provide server-side functionality to the patient device 102. By way of example, the preference subsystem 202 may be deployed in both the patient device 102 and the benefit manager device 106. The patient device 102 may then perform some of the functionality while other functionality is performed by the benefit manager device 106.

Figure 4:
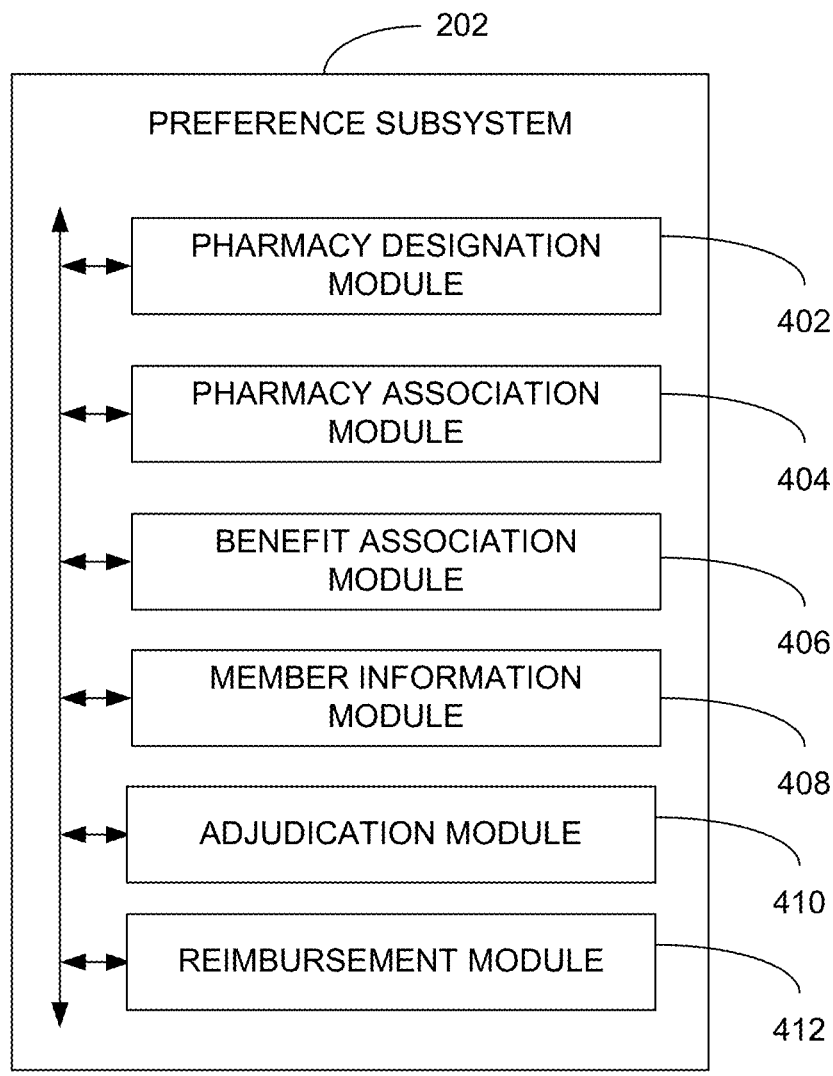
FIG. 4 is a block diagram of an example preferred pharmacy subsystem that may be deployed within the patient device of FIG. 2 or the benefit manager device of FIG. 3, according to an example embodiment.

FIG. 4 illustrates an example the preference subsystem 202 that may be deployed in the patient device 102, the benefit manager device 106, or otherwise deployed in another system. One or more modules are communicatively coupled and included in the preference subsystem 202 to enable the designation of a preferred pharmacy and/or pharmacist for the member and/or the association of benefits with the preferred pharmacy and/or pharmacist and the member. The modules of the preference subsystem 202 that may be included are a pharmacy designation module 402, a pharmacy association module 404, a benefit association module 406, a member information module 408, an adjudication module 410, and a reimbursement module 412.

In some embodiments, the modules of the preference subsystem 202 may be distributed so that some of the modules are deployed in the patient device 102 and/or the pharmacy device and some modules are deployed in the benefit manager device 106. In one embodiment, the modules are deployed in memory and executed by a processor coupled to the memory. The functionality contained within the modules 402-412 may be combined into a lesser number of modules, further divided among a greater number of modules, or redistributed among existing modules. Other configurations including the functionality of the modules 402-412 may be used.

In an embodiment, the pharmacy designation module 402 may receive a designation of a pharmacy and/or pharmacist within a pharmacy network as a preferred pharmacy and/or pharmacist. In an embodiment, the designation of a pharmacy as a preferred pharmacy may include a designation of a single, or particular, retail pharmacy (and/or a particular chain of pharmacies) from among a plurality of retail pharmacies (e.g., which may include a plurality of independent and/or chain retail pharmacies). For example, a drug benefit program provided by a PBM for a member may include one, or more than one, network of pharmacies at which members of the drug benefit program may fill prescriptions, with at least a portion of the cost of the prescription being covered by the drug benefit program. A member of the drug benefit program may designate a particular retail pharmacy (and/or a set of pharmacies) as being a preferred pharmacy, which the member wishes to predominantly use for filling prescriptions. The pharmacy that the member designates as being his or her preferred pharmacy may, for example, include a pharmacy within the pharmacy network covered by the drug benefit program that is geographically convenient (e.g., local the member's home or office, etc.), or other pharmacy for which the member has some affinity. In some embodiments, the preferred pharmacy designation may include the designation of a particular pharmacist (and/or a set of pharmacists) as being a preferred pharmacist. In some embodiments, the particular pharmacist may be identified, e.g., based on a license number associated with the pharmacist, and/or other suitable form of identification.

In an embodiment, the member may designate the pharmacy and/or pharmacist as being the member's preferred pharmacy via a computer interface, for example a website provided by the PBM, by way of an e-mail response, or other suitable computer interface. In such an example, the pharmacy designation module 402 may receive the designation of the pharmacy as being the member's preferred pharmacy from the patient device 102 through the network 104, or otherwise. In some embodiments, the member may designate the pharmacy as being the member's preferred pharmacy in other ways, such as through a mailed or telephoned in response, a designation made at the preferred pharmacy itself, or in another suitable manner. The designation of the pharmacy as being the member's preferred pharmacy and/or pharmacist may be communicated to the PBM and may be received by the pharmacy designation module 402 (e.g., via an automated telephone system, entry into a PBM system, such as the benefit manager device 106, by a customer service representative, etc.).

In an embodiment, the preferred pharmacy may include any pharmacy of the member's choosing, any pharmacy within a pharmacy network identified by the PBM, and/or may include a pharmacy identified by the PBM as being an eligible preferred pharmacy. In an embodiment in which a member may designate a preferred pharmacy from a list of eligible pharmacies, the pharmacy designation module 402 may generate a list of eligible pharmacies from which the member may select a preferred pharmacy. In such an embodiment, the pharmacy designation module 402 may receive the designation of the preferred pharmacy in response to generating the list of eligible pharmacies. The list of eligible pharmacies may be generated based on various criteria. For example, the list of eligible pharmacies may be generated based on threshold experience and qualifications of one, or more than one, pharmacists employed by the pharmacy (e.g., based on the pharmacist having a qualifying degree from a qualifying college), the ability of the pharmacy to administer additional services (e.g., blood pressure screenings, blood sugar screenings, cholesterol screenings, etc.), and/or various other factors or considerations. In an embodiment, one, or more than one, of the pharmacies on the list of eligible pharmacies may include an associated rating. The rating associated with the pharmacies may be based on qualitative and/or quantitative criterion, such as pricing comparisons, user reviews, reviews by consumer organizations, or the like.

In some embodiments, once a preferred pharmacy and/or pharmacist has been designated, the member may be permitted to periodically designate a new pharmacy and/or pharmacist as being preferred. For example, the member may be permitted to designate a new preferred pharmacy on an annual basis, a semi-annual basis, or other suitable periodic basis. In some embodiments, the member may be permitted to designate a new preferred pharmacy upon the occurrence of an event, such a change of an address associated with the member, a change of an employer associated with the member, departure of a preferred pharmacist, or other suitable event.

In an embodiment, the pharmacy association module 404 may associate the preferred pharmacy and/or pharmacist with the member. For example, the member data 112 may include one or more member attributes (e.g., a member profile). The pharmacy association module 404 may store an association between the member and preferred pharmacy designated by the member within the member data 112. In some embodiments, the pharmacy association module 404 may otherwise associate the member and the preferred pharmacy designated by the member.

A set of preferred pharmacy benefits (and/or preferred pharmacist benefits) may be associated with the member and the preferred pharmacy and/or pharmacist by the benefit association module 406. For example, in an embodiment, the benefits that the member may receive under the drug benefit program at the preferred pharmacy may be different than the benefits that the member may be receive at other pharmacies within the pharmacy network (e.g., which may include pharmacies at which the member may receive at least some coverage under the drug benefit program). In an embodiment, the set of preferred pharmacy benefits may be better (e.g., more advantageous for one or more of the member, the pharmacy, the PBM, and the client) some regard than the set of benefits that the member may receive under the drug benefit program at other pharmacies. In some embodiments, e.g., in which the drug benefit program may include more than one pharmacy network, additional sets of benefits may be associated with pharmacies within each network, which may each differ at least in some regard from the benefits that the member may receive at the preferred pharmacy. In such an embodiment, the benefit association module 406 may associate a set of non-preferred benefits with another pharmacy within the pharmacy network, e.g., thereby associating different benefits with the preferred pharmacy and with all other pharmacies within the pharmacy network.

In an embodiment, the preferred pharmacy benefits may include preferred prescription coverage. Preferred prescription coverage may include, for example, a lower co-pay required by the member, lower out-of-pocket cost to the member, a lower deductible for the member, and/or preferred pricing for prescriptions and/or over the counter drugs. In some embodiments, the preferred pharmacy benefits may include, for example, the ability for the member to receive extended prescriptions (e.g., prescription fills including 90 days worth of medication) as compared to prescriptions received at non-preferred pharmacies (e.g., prescriptions fills including 30 days worth of medication). In an embodiment, the preferred prescription coverage may include coverage for additional and/or different drugs. In an embodiment, the preferred pharmacy benefits may include additional service coverage. In an example embodiment, the additional service coverage may include coverage under the drug benefit program for vaccinations, such a flu shots, received at the preferred pharmacy, medication therapy management services and/or consultations, and/or other additional services.

In some embodiments, the preferred pharmacy benefits may include, for example, incentives provided to the member for using the preferred pharmacy. For example, the member may receive customer reward points associated with user of the preferred pharmacy (e.g., use of the preferred pharmacy for filling prescriptions and/or for other services and/or products purchased at the preferred pharmacy). The customer reward points may, for example, be used by the member for additional discounts at the preferred pharmacy, reductions in co-pays for prescriptions fill at the preferred pharmacy, for health screenings, etc.

In some embodiments, the preferred pharmacy benefits may include availability of an adherence device to the member. The adherence device may be provided a reduced cost or free of cost to the member. Examples of adherence devices include smart caps, reminder devices, and the like.

In some embodiments, the member information module 408 may generate preferred pharmacy member information, and may transmit the preferred pharmacy information to the preferred pharmacy. For example, the preferred pharmacy member information may include information about the member that may allow the preferred pharmacy to provide a higher level of service or care to the member. Examples of preferred pharmacy member information may include member prescription history, therapies that the member is currently undergoing, medical concerns associated with the member (e.g., high blood pressure, high cholesterol, etc.). In an embodiment, generating the preferred pharmacy member information may include accessing the member data 112 from the database 110. In an embodiment, the member information module 408 may provide the pharmacy with a portal for accessing the generated preferred pharmacy member information, e.g., by the pharmacy device 108 through the network 104.

In an embodiment, the adjudication module 410 may adjudicate a pharmacy claim based on an applicable set of pharmacy benefits for the member and the pharmacy submitting the pharmacy claim. For example, the adjudication module 410 may adjudicate a pharmacy claim from the preferred pharmacy for a prescription or additional service for the member using the set of preferred pharmacy benefits. In an embodiment, the pharmacy claim may be a pharmacy claim for a first fill of a prescription (or first rendering of an additional service, etc.), or the pharmacy claim may be a pharmacy claim for a refill of a prescription (or subsequent rendering of the additional service, etc.). Similarly, the adjudication module 410 may adjudicate a pharmacy claim from another pharmacy (i.e., a pharmacy that is not the member's designated preferred pharmacy) using the benefits for non-preferred pharmacies. In an embodiment, adjudicating the pharmacy claim may include determining if the pharmacy submitting the pharmacy claim is the designated preferred pharmacy for the member. Determining if the pharmacy submitting the pharmacy claim is the designated preferred pharmacy for the member may include accessing the member data 112 and identifying an association between the member and preferred pharmacy designated by the member within the member data 112. In an embodiment, the adjudication module 410 may access the applicable set of pharmacy benefits based on whether the pharmacy submitting the pharmacy claim is designated as a preferred pharmacy for the member in the member data. In an embodiment, the adjudication module 410 may receive the applicable set of pharmacy benefits from the benefit association module 406, the member information module 408, and/or the member data 112.

In some embodiments, pharmacy claims for the member may be adjudicated based on the designation of the preferred pharmacy by the member (e.g., may be adjudicated according to the set of preferred pharmacy benefits). For example, in an embodiment in which the member may be required to pay a lower co-pay associated with prescriptions filled at the preferred pharmacy, a pharmacy claim for a prescription for the member filled at the preferred pharmacy may be adjudicated indicating the lower co-pay. In some embodiments, in which additional services (e.g., health screenings, such as blood pressure screenings, blood sugar screenings, cholesterol screenings, etc.) may be covered for the member at the preferred pharmacy, pharmacy claims for such additional services at the preferred pharmacy may be adjudicated on the basis of the designation of the preferred pharmacy by the member. For example, such additional services may be covered under the drug benefit program associated with the member. Pharmacy claims from pharmacies other than the preferred pharmacy may be adjudicated based on the set of non-preferred pharmacy benefits. Adjudicating pharmacy claims based on the set of non-preferred pharmacy benefits may, for example, require that the member pay a higher co-pay, that coverage for additional services may be denied under the drug benefit program, or the like.

In an embodiment, a preferred pharmacy reimbursement rate may be associated with the preferred pharmacy by the reimbursement module 412 for pharmacy claims associated with the member. In an embodiment, the reimbursement module 412 may also allocate reimbursement funds to the preferred pharmacy for a pharmacy claim for the member based on the preferred pharmacy reimbursement rate. For example, the reimbursement module 412 may determine a reimbursement rate for prescriptions filled by the preferred pharmacy for the member. In an embodiment, the reimbursement rate for prescriptions filled by the member at the preferred pharmacy may be less than reimbursement rates paid to non-preferred pharmacies for prescriptions filled by the member. For example, based on the member designation of the pharmacy as being a preferred pharmacy for the member, it may be anticipated that a member may fill a certain number of prescriptions at the preferred pharmacy, giving rise to a probable volume of business for the preferred pharmacy, thereby allowing the PBM to negotiate a more favorable (e.g., lower) reimbursement rate. In some embodiments, if more than a single member (e.g., either within a single drug benefit program or within more than one drug benefit program provided by the PBM) designates the pharmacy as a preferred pharmacy, the aggregate number of members may provide a probability of a greater volume of business for the pharmacy, thereby potentially allowing even more favorable reimbursement rates to be negotiated between the pharmacy and the PBM. In some embodiments, favorable reimbursement rates may be negotiated between the preferred pharmacy and the PBM on the likelihood that, as the preferred pharmacy for the member, the preferred pharmacy will receive ancillary business from the member, e.g., for over the counter drugs, therapy management, and the like.

Figure 5:
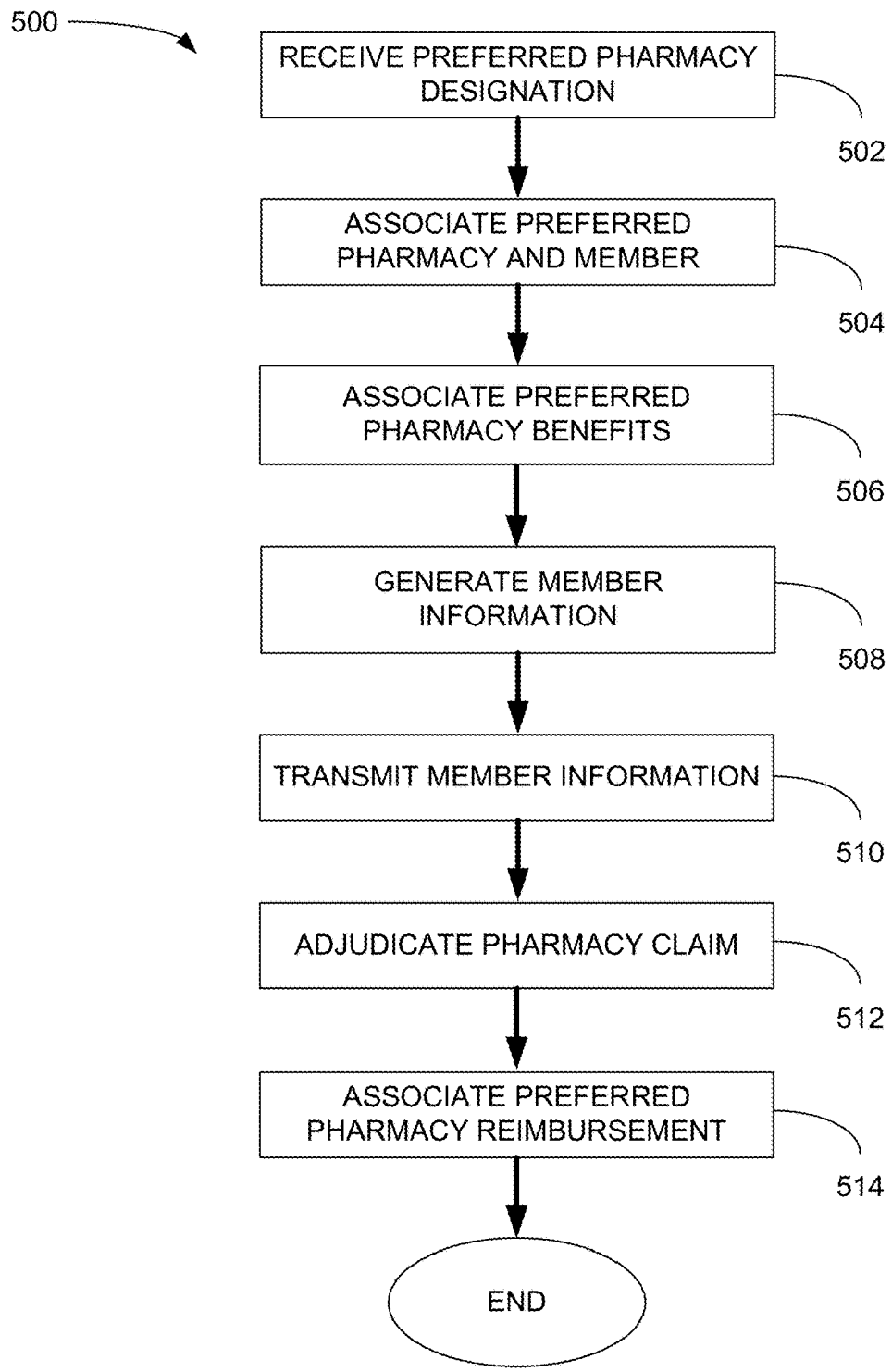
FIG. 5 is a process flow illustrating a method for preferred pharmacy designation, according to an example embodiment.

FIG. 5 illustrates a method 500 for member preferred pharmacy designation, according to an example embodiment. The method 500 may be performed by the patient device 102, by the benefit manager device 106, partially by the patient device 102 and partially be the benefit manager device 106, or may be otherwise performed.

A designation of a pharmacy within a pharmacy network as being a preferred pharmacy may be received at block 502. The designation may be received from the patient device 102 through network 104, or may be otherwise received. The designation of the preferred pharmacy may indicate the pharmacy that the member wishes to use as their primary pharmacy. In some embodiments, the designated pharmacy may include any particular retail pharmacy (or in some embodiments a particular pharmacist) included within a pharmacy network of the drug benefit program of the member. In some embodiments, the preferred pharmacy may be selected from a list of one or more eligible pharmacies.

In response to receiving the designation of the preferred pharmacy, the preferred pharmacy may be associated with the member at block 504. In some embodiments, the association between the member and the preferred pharmacy may be stored in the member data 112, for example in a member profile associated with the member.

Preferred pharmacy benefits may be associated with the member and the preferred pharmacy at block 506. In some embodiments, the preferred pharmacy benefits, which the member may receive when utilizing the preferred pharmacy may be different in at least some regard from the benefits the member receives when utilizing a pharmacy other than the preferred pharmacy. Examples of preferred pharmacy benefits may include lower co-pay, preferred prescription pricing, coverage for certain services (e.g., vaccinations, health screenings, etc.) and the like. In some embodiments, the different (e.g., non-preferred pharmacy) benefits may be associated with pharmacies other than the preferred pharmacy.

Preferred pharmacy member information may be generated and transmitted to the preferred pharmacy at block 510. The preferred pharmacy member information may include information about the member that may be relevant to the preferred pharmacy for providing a greater level of member service or quality of care. Examples of preferred pharmacy member information may include member prescription history, member health concerns, therapies the member is currently (or has previously) undergoing. In some embodiments, the member information may be transmitted to the pharmacy by providing a preferred pharmacy portal via which the preferred pharmacy member information may be accessed (by the pharmacy device 108 through the network 104, for example).

A pharmacy claim may be adjudicated at block 512. In some embodiments, an adjudication request associated with a prescription, or an additional service, for a member may then be received. The adjudication request may include, for example, the pharmacy claim itself, or another request to adjudicate a pharmacy claim that may accompany the pharmacy claim and/or be separately received. The pharmacy claim may include a pharmacist identifier (e.g., based on designation of a preferred pharmacist) and/or pharmacy identifier (e.g., based on designation of a preferred pharmacy). Based on the pharmacist identifier and/or the pharmacy identifier, a claim for a prescription drug indicated by the prescription, or for an additional service, may be adjudicated in accordance with the set pharmacy benefits (e.g., either the set of preferred pharmacy benefits or one or more sets of pharmacy benefits associated with other pharmacies). In an embodiment, adjudicating the pharmacy claim may include determining if the pharmacy submitting the claim is the designated preferred pharmacy for the member, for example by accessing the member data. In an embodiment, adjudicating the pharmacy claim may also include accessing the applicable set of pharmacy benefits (e.g., by accessing the database 110, receiving the set of benefits from another device, or the like).

A preferred pharmacy reimbursement rate may be associated with the preferred pharmacy at block 514. For example, based on the designation of the pharmacy as being a preferred pharmacy for the member, a preferred pharmacy reimbursement rate may be negotiated between the preferred pharmacy and the PBM. In such an embodiment, the preferred pharmacy reimbursement rate may be associated with the preferred pharmacy and the member, such that claims by the pharmacy, and associated with the member, may be reimbursed at the preferred pharmacy reimbursement rate.

Figure 6:
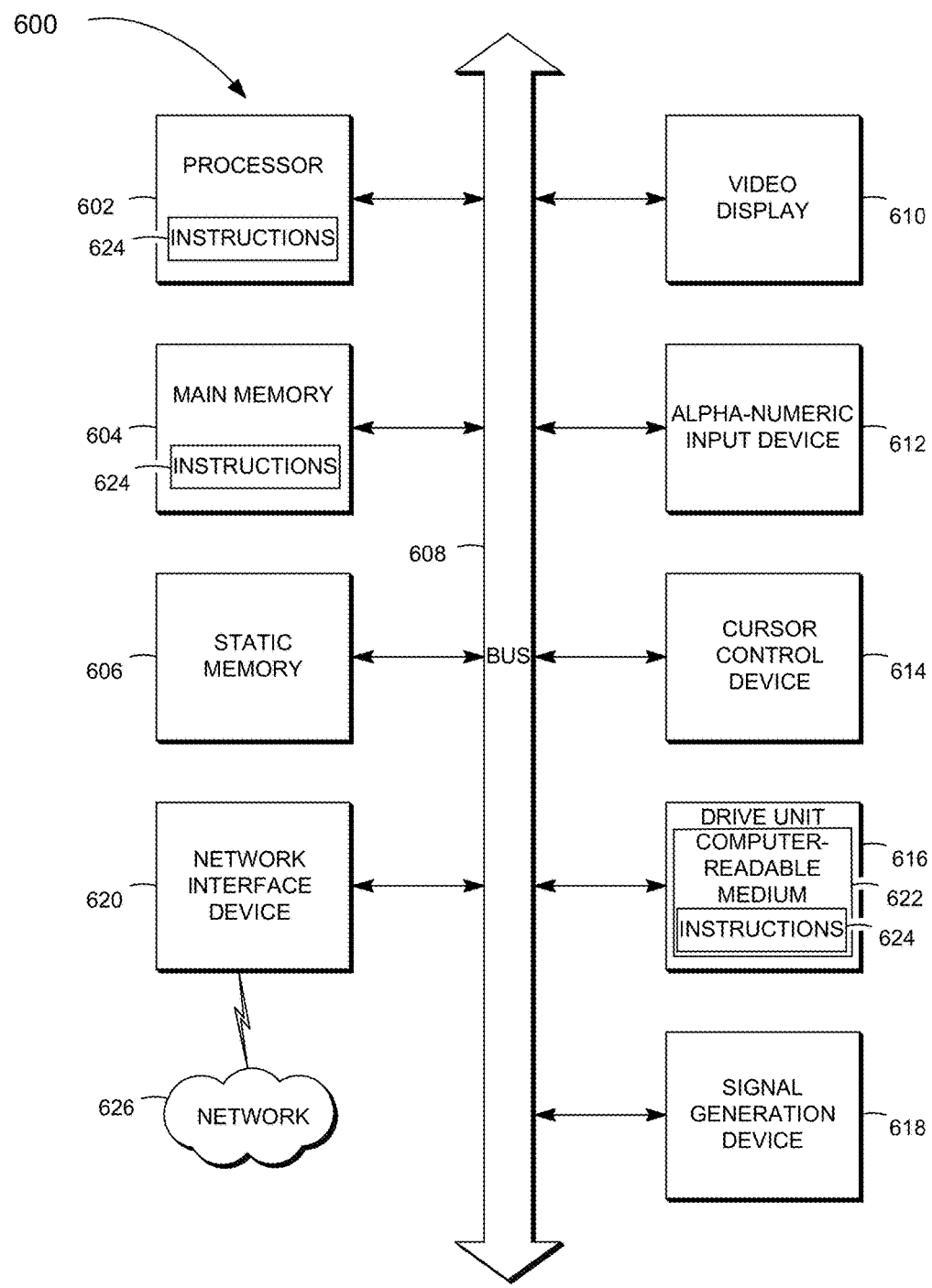
FIG. 6 is a block diagram of a machine in the example form of a computer system within which a set of instructions for causing the machine to perform any one or more of the methodologies discussed herein may be executed or stored.

FIG. 6 shows a block diagram of a machine in the example form of a computer system 600 within which a set of instructions may be executed causing the machine to perform any one or more of the methods, processes, operations, or methodologies discussed herein. The patient device 102, the benefit manager device 106, and/or the pharmacy device 108 may include the functionality of the one or more computer systems 600.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 600 includes a processor 602 (e.g., a central processing unit (CPU) a graphics processing unit (GPU) or both), a main memory 604 and a static memory 606, which communicate with each other via a bus 608. The computer system 600 further includes a video display unit 610 (e.g., a liquid crystal display (LCD) or a cathode ray tube (CRT)). The computer system 600 also includes an alphanumeric input device 612 (e.g., a keyboard), a cursor control device 614 (e.g., a mouse), a drive unit 616, a signal generation device 618 (e.g., a speaker) and a network interface device 620.

The drive unit 616 includes a computer-readable medium 622 on which is stored one or more sets of instructions (e.g., software 624) embodying any one or more of the methodologies or functions described herein. The software 624 may also reside, completely or at least partially, within the main memory 604 and/or within the processor 602 during execution thereof by the computer system 600, the main memory 604 and the processor 602 also constituting computer-readable media.

The software 624 may further be transmitted or received over a network 626 via the network interface device 620.

While the computer-readable medium 622 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a designation of a pharmacy within a pharmacy network may be received as a preferred pharmacy designation. The preferred pharmacy designation may be associated with a member. A set of preferred pharmacy benefits may be associated with the member and the preferred pharmacy designation. A pharmacy claim associated with the preferred pharmacy designation for a prescription for the member may be adjudicated based on the set of preferred pharmacy benefits.

In an example embodiment, a designation of a pharmacist within a pharmacy network may be received as a preferred pharmacist designation. The preferred pharmacist designation may be associated with a member. A set of preferred pharmacist benefits may be associated with the member and the preferred pharmacist designation. A pharmacy claim associated with the preferred pharmacist designation for a prescription for the member may be adjudicated based on the set of preferred pharmacist benefits.

Thus, methods and systems for designating a preferred pharmacy for a member have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
   producing a list of eligible pharmacies within a pharmacy network available to a member at a processor of a preference subsystem of a pharmacy benefit device;
   reducing the list of eligible pharmacies by selecting pharmacies that meet a client criteria and having a first benefit to the member different than a second benefit at another one of the pharmacies, wherein the first benefit includes adherence devices at each of the pharmacies on the list of eligible pharmacies;
   sending the reduced list of eligible pharmacies within the pharmacy network to a member device to display on the member device including the list of eligible pharmacies;
   displaying the reduced list of eligible pharmacies within the pharmacy network on the member device;
   selecting member designation of a pharmacy from the reduced list of eligible pharmacies on the member device;
   periodically receiving, on the processor of the preference subsystem of the pharmacy benefit device, the member designation of a pharmacy within the pharmacy network and on the reduced list of eligible pharmacies available to the member as a member-preferred pharmacy designation;
   storing, on the pharmacy benefit device, the member-preferred pharmacy designation with a member;
   linking the member-preferred pharmacy designation to a member profile;
   assigning a set of preferred pharmacy benefits for the member to the member profile;
   after assigning the set of preferred pharmacy benefits, receiving, on the processor of the pharmacy benefit device from a member-preferred pharmacy identified by the member-preferred pharmacy designation through a network, an adjudication request associated with the member-preferred pharmacy designation for a prescription for the member;
   adjudicating, on the processor of the pharmacy benefit device using the received adjudication request, a pharmacy claim associated with the member-preferred pharmacy designation for the prescription for the member based on the set of preferred pharmacy benefits assigned to the member profile;
   transmitting, from a benefit manager device over a network, an adjudication response from adjudicating based on adjudication of the pharmacy claim;
   receiving, at a pharmacy device associated with the member-preferred pharmacy, the adjudication response; and
   dispensing the prescription with a tangible prescription drug for the member at the member-preferred pharmacy after receipt of the adjudication response associated with the member and the member-preferred pharmacy designation.

2. The method of claim 1, further comprising:
   determining a pharmacy location associated with the pharmacy claim;

determining whether the member-preferred pharmacy designation includes the pharmacy location, wherein adjudication of the pharmacy claim is based on the set of preferred pharmacy benefits and a determination that the member-preferred pharmacy designation includes the pharmacy location.

3. The method of claim 1, wherein sending the list of eligible pharmacies includes displaying the list of eligible pharmacies, and wherein receiving the member-preferred pharmacy designation is responsive to generating a list of eligible preferred pharmacies and the member-preferred pharmacy designation is a single pharmacy in the list of eligible preferred pharmacies.

4. The method of claim 1, further comprising:
associating a set of non-preferred pharmacy benefits with a second pharmacy of the other pharmacies within the pharmacy network;
adjudicating, at the pharmacy benefit device, an additional pharmacy claim by the second pharmacy for a prescription for the member based on the set of non-preferred pharmacy benefits;
transmitting a second adjudication response over the network based on adjudication of the additional pharmacy claim; and
filling the prescription for the member at the second pharmacy after transmission of the second adjudication.

5. The method of claim 1, wherein the preferred pharmacy benefits include preferred prescription coverage.

6. The method of claim 1, wherein the preferred pharmacy benefits include extended prescription coverage.

7. The method of claim 1, wherein the preferred pharmacy benefits include additional service coverage including at least one of medical services and reward points,
wherein the preferred pharmacy benefits at the member-preferred pharmacy designation are different than pharmacy benefits for the member at another pharmacy;
wherein adjudicating includes adjudicating the additional services for the member at the associated member-preferred pharmacy; and
wherein the associated the member-preferred pharmacy designation with the member includes automatically opening a pharmacy portal between the pharmacy benefit device and the pharmacy device associated with the member-preferred pharmacy to access preferred pharmacy member at the pharmacy device.

8. The method of claim 1, further comprising:
generating preferred pharmacy member information; and
transmitting the preferred pharmacy information to the member-preferred pharmacy.

9. The method of claim 1, further comprising:
associating a preferred pharmacy reimbursement rate with the pharmacy claim associated with the member from the member-preferred pharmacy.

10. The method of claim 9, further comprising:
allocating reimbursement funds to the member-preferred pharmacy based on the preferred pharmacy reimbursement rate.

11. The method of claim 1, wherein the designation of the pharmacy within a pharmacy network is a member designation of a single retail pharmacy among a plurality of retail pharmacies.

12. The method of claim 1, wherein the preferred pharmacy benefits include at least one of preferred prescription coverage, extended prescription coverage, and additional service coverage and further includes rewards from the member-preferred pharmacy.

13. The method of claim 1, wherein adjudicating includes automatically selecting, using the processor of the pharmacy benefit device, a lower co-pay with the member using the member-preferred pharmacy in place of at least one non-member-preferred pharmacy in the pharmacy network and selecting a higher co-pay with the member using the at least one non-member-preferred pharmacy in the pharmacy network.

14. The method of claim 1, wherein the pharmacy network is part of preferred pharmacies participating in a drug benefit program provided by a benefits manager.

15. A non-transitory machine-readable medium comprising instructions, which, when executed by one or more processors, cause the one or more processors to perform the following operations:
producing a list of eligible pharmacies within a pharmacy network available to a member at a processor of a preference subsystem of a pharmacy benefit device using various criteria set by a client, with at least one of the pharmacies having a different benefit to the member than another one of the pharmacies, wherein producing includes filtering the pharmacy network using client criteria, benefit and member criteria to output the list of eligible pharmacies;
sending the list of eligible pharmacies within the pharmacy network to a member device for display on the member device;
periodically receiving, on a processor at a pharmacy benefit device, a member designation of a pharmacy within a pharmacy network as a member-preferred pharmacy designation;
linking, on the processor at the pharmacy benefit device, the member-preferred pharmacy designation with a member to a member profile;
assigning, using the processor at the pharmacy benefit device, a set of preferred pharmacy benefits for the member to the member profile;
after assigning the set of preferred pharmacy benefits, receiving, on the processor at the pharmacy benefit device from the member-preferred pharmacy identified by the member-preferred pharmacy designation through a network, an adjudication request associated with the member-preferred pharmacy designation for a prescription for the member; and
adjudicating, on the processor at the pharmacy benefit device using the adjudication request, a pharmacy claim associated with the member-preferred pharmacy designation for the prescription for the member based on the set of preferred pharmacy benefits assigned to the member profile; and
transmitting, from the pharmacy benefit device over a network, an adjudication response from adjudicating the pharmacy claim to the member-preferred pharmacy designation for dispensing a tangible prescription drug according to the prescription and the set of preferred pharmacy benefits,
wherein the linking the member-preferred pharmacy designation with the member includes automatically opening a pharmacy portal between the pharmacy benefit device and the pharmacy device associated with the member-preferred pharmacy to generate preferred pharmacy member at the pharmacy device.

16. The non-transitory machine-readable medium of claim 15, further comprising instructions for:
determining a pharmacy location associated with the pharmacy claim;

determining whether the member-preferred pharmacy designation includes the pharmacy location,
wherein adjudication of the pharmacy claim is based on the set of preferred pharmacy benefits and a determination that the member-preferred pharmacy designation includes the pharmacy location.

17. The non-transitory machine-readable medium of claim 15, wherein receiving the member-preferred pharmacy designation is responsive to generating a list of eligible preferred pharmacies.

18. The non-transitory machine-readable medium of claim 15, further comprising instructions for:
associating a set of non-preferred pharmacy benefits with a second pharmacy within the pharmacy network; and
adjudicating an additional pharmacy claim by the second pharmacy for a prescription for the member based on the set of non-preferred pharmacy benefits.

19. The non-transitory machine-readable medium of claim 15, wherein the preferred pharmacy benefits include preferred prescription coverage.

20. The non-transitory machine-readable medium of claim 15, wherein the preferred pharmacy benefits include extended prescription coverage.

21. The non-transitory machine-readable medium of claim 15, wherein the preferred pharmacy benefits include additional service coverage.

22. The non-transitory machine-readable medium of claim 15, further comprising instructions for:
generating preferred pharmacy member information; and
transmitting the preferred pharmacy information to the member-preferred pharmacy.

23. The non-transitory machine-readable medium of claim 15, further comprising instructions for:
associating a preferred pharmacy reimbursement rate with the pharmacy claim associated with the member from the member-preferred pharmacy.

24. The non-transitory machine-readable medium of claim 23, further comprising instructions for:
allocating reimbursement funds to the member-preferred pharmacy based on the preferred pharmacy reimbursement rate.

25. The non-transitory machine-readable medium of claim 15, wherein the member designation of the pharmacy within a pharmacy network is a designation of a single retail pharmacy among a plurality of retail pharmacies.

26. A method comprising:
producing a list of eligible pharmacies within a pharmacy network available to a member at a processor of a preference subsystem of a pharmacy benefit device using various criteria set by a client, with at least one of the pharmacies having a different benefit to the member than another one of the pharmacies, wherein producing includes filtering the pharmacy network using client criteria, benefit, adherence criteria and member criteria to output the list of eligible pharmacies;
sending the list of eligible pharmacies within the pharmacy network to a member device for display on the member device with the list of eligible pharmacies;
periodically receiving, on a processor at a pharmacy benefit device, a member-designation of a pharmacist within a pharmacy network as a member-preferred pharmacist designation, wherein the pharmacy network is stored in the at the pharmacy benefit device;
linking, on the processor at the pharmacy benefit device, the member-preferred pharmacist designation with a member a member profile;
assigning, on the processor at the pharmacy benefit device, a set of preferred pharmacist benefits for the member with the member profile;
automatically opening a pharmacy portal between the pharmacy benefit device and the pharmacy device associated with the member-preferred pharmacy to generate preferred pharmacy member at the pharmacy device;
after assigning the set of preferred pharmacist benefits, adjudicating, on the processor at the pharmacy benefit device using an adjudication request from the member-preferred pharmacist designation, a pharmacy claim associated with the member-preferred pharmacist designation for a prescription for the member based on the set of preferred pharmacist benefits;
transmitting an adjudication from the adjudicating at the pharmacy benefit device to the member-preferred pharmacist designation; and
dispensing the prescription with a tangible prescription drug at a pharmacy identified with the member-preferred pharmacist designation.

27. A pharmacy system comprising
a preference subsystem to receive a member designation of a pharmacy within a client-limited pharmacy network available to a member as a member-preferred pharmacy designation from a member device that displays the pharmacies in the pharmacy network, to associate the member-preferred pharmacy designation with a member profile by storing the designation in a computer memory storing the member profile, and to associate a set of preferred pharmacy benefits with the member and the member-preferred pharmacy designation to the member profile, storing the preferred benefits in the member profile, wherein the set of preferred pharmacy benefits are better than a benefit available at other pharmacies in the pharmacy network available to the member, wherein the client-limited pharmacy network providing a reduced list of all pharmacies to a member device on which the member-preferred pharmacy designation is made;
an adjudication subsystem to receive, after the preference subsystem associates the set of preferred pharmacy benefits, an adjudication request associated with the member-preferred pharmacy designation for a prescription for the member, wherein the adjudication subsystem is to adjudicate a pharmacy claim associated with the member-preferred pharmacy designation for the prescription for the member based on the set of preferred pharmacy benefits associated with the member and the member-preferred pharmacy designation;
a transmission subsystem to transmit over a network an adjudication response from the adjudication subsystem based on adjudication of the pharmacy claim and to transmit a member portal to the member-preferred pharmacy including at least the set of preferred pharmacy benefits;
a receiver subsystem to receive, at a pharmacy device associated with a member-preferred pharmacy, the adjudication response; and
the member-preferred pharmacy is to dispense a tangible drug to fill the prescription for the member after receipt of the adjudication response associated with the member and the member-preferred pharmacy designation.

* * * * *